United States Patent
Turek et al.

(10) Patent No.: US 8,925,549 B2
(45) Date of Patent: Jan. 6, 2015

(54) FLOW CONTROL ADAPTER FOR PERFORMING SPIROMETRY AND PULMONARY FUNCTION TESTING

(75) Inventors: Joseph William Turek, Durham, NC (US); Eric Miguel Toloza, Durham, NC (US)

(73) Assignee: Surge Ingenuity Corporation, Batavia, IL (US)

( * ) Notice: Subject to any disclaimer, the term of this patent is extended or adjusted under 35 U.S.C. 154(b) by 1232 days.

(21) Appl. No.: 12/539,534

(22) Filed: Aug. 11, 2009

(65) Prior Publication Data

US 2010/0031964 A1 Feb. 11, 2010

Related U.S. Application Data

(60) Provisional application No. 61/087,893, filed on Aug. 11, 2008.

(51) Int. Cl.
| | |
|---|---|
| A61M 15/00 | (2006.01) |
| A61M 16/00 | (2006.01) |
| A62B 7/00 | (2006.01) |
| A62B 9/00 | (2006.01) |
| A62B 18/00 | (2006.01) |
| A62B 9/02 | (2006.01) |
| A62B 9/06 | (2006.01) |
| A61B 5/05 | (2006.01) |
| A61M 16/08 | (2006.01) |
| A61B 5/087 | (2006.01) |
| A61B 5/097 | (2006.01) |
| A61B 5/091 | (2006.01) |
| A61M 16/04 | (2006.01) |
| A61M 16/20 | (2006.01) |

(52) U.S. Cl.
CPC .......... *A61M 16/0816* (2013.01); *A61B 5/0873* (2013.01); *A61B 5/097* (2013.01); *A61M 16/0833* (2013.01); *A61B 5/091* (2013.01); *A61M 16/0465* (2013.01); *A61M 16/208* (2013.01); *A61M 2016/0027* (2013.01); *A61M 2205/3368* (2013.01); *A61M 2205/502* (2013.01); *A61M 2205/583* (2013.01)

USPC .......... 128/207.16; 128/200.24; 128/205.24; 128/207.14; 600/358

(58) Field of Classification Search
CPC .......... A61M 2016/0833; A61B 5/087; A61B 5/0875; A61B 5/091; A61B 5/097
USPC ............. 128/200.24, 205.24, 206.15, 207.12, 128/201.28, 203.11; 600/538–541
See application file for complete search history.

(56) References Cited

U.S. PATENT DOCUMENTS 3,028,873 A * 4/1962 Kindred .................. 137/512
3,319,624 A * 5/1967 Arp et al. .................. 600/541

(Continued)

OTHER PUBLICATIONS

The Ohio State University Medical Center, Aug. 2005, Department of Respiratory Therapy: The Ohio State University Medical Center, Edition 1, p. 1-2.*

(Continued)

*Primary Examiner* — Lynne Anderson
*Assistant Examiner* — Bradley Philips
(74) *Attorney, Agent, or Firm* — Seed IP Law Group PLLC

(57) ABSTRACT

A breathing circuit for a tracheostomized patient provides respiratory care and pulmonary function testing. The breathing circuit includes a flow control adapter that directs an inspiratory flow of air and an expiratory flow of air. The flow control adapter includes a subject port for coupling to a tracheostomy tube, an inspiratory port for coupling to an incentive spirometer, and an expiratory port. The flow control adapter further includes an adapter body and a one-way valve. The adapter body is configured to define an inspiratory fluid flow path between the inspiratory port and the subject port and to define an expiratory fluid flow path between the subject port and the expiratory port. The one-way valve substantially prevents air that flows generally along the inspiratory fluid flow path from flowing through the expiratory port during inspiration and allows air flowing generally along the expiratory fluid flow path to flow through the expiratory port during expiration.

13 Claims, 7 Drawing Sheets

(56) References Cited

U.S. PATENT DOCUMENTS

| | | | | |
|---|---|---|---|---|
| 3,949,737 | A | * | 4/1976 | Nielsen .................. 600/539 |
| 3,967,619 | A | * | 7/1976 | Story et al. ............... 128/205.13 |
| 4,188,946 | A | * | 2/1980 | Watson et al. ............ 128/204.22 |
| 4,211,240 | A | | 7/1980 | Gallagher |
| 4,787,655 | A | * | 11/1988 | Gross et al. ................ 285/127.1 |
| 5,050,593 | A | * | 9/1991 | Poon ........................ 128/204.23 |
| 5,522,380 | A | * | 6/1996 | Dwork .................... 128/200.23 |
| 5,735,271 | A | | 4/1998 | Lorenzen et al. |
| 6,041,777 | A | * | 3/2000 | Faithfull et al. .......... 128/200.24 |
| 6,095,140 | A | * | 8/2000 | Poon et al. ............... 128/204.26 |
| 6,209,539 | B1 | | 4/2001 | Loescher et al. |
| 7,946,291 | B2 | * | 5/2011 | Fink et al. ................. 128/203.12 |
| 2005/0229928 | A1 | * | 10/2005 | Ivri et al. .................. 128/203.12 |
| 2007/0186928 | A1 | * | 8/2007 | Be'Eri ..................... 128/204.18 |
| 2010/0076332 | A1 | * | 3/2010 | Tolmie et al. ................. 600/538 |
| 2011/0259339 | A1 | * | 10/2011 | Isaza ....................... 128/207.16 |

OTHER PUBLICATIONS

"Discharge Instructions: Using an Incentive Spirometer with Your Tracheostomy Tube," Northern Inyo Hospital, Krames Patient Education, Dec. 14, 2007, 2 pages.

Tan, "Incentive Spriometry for Tracheostomy and Laryngectomy Patients," The Journal of Otolaryngology, 24(5):292-294, 1995.

\* cited by examiner

FLOW CONTROL ADAPTER FOR PERFORMING SPIROMETRY AND PULMONARY FUNCTION TESTING

CROSS-REFERENCE TO RELATED APPLICATION

This application claims the benefit under 35 U.S.C. §119 (e) of U.S. Provisional Patent Application No. 61/087,893 filed Aug. 11, 2008. This provisional application is incorporated herein by reference in its entirety.

BACKGROUND

1. Technical Field

The present invention relates generally to flow control adapters for performing respiratory therapy, and in particular, to flow control adapters for performing incentive spirometry and pulmonary function testing in tracheostomized patients.

2. Description of the Related Art

Tracheostomies are often performed to provide direct access to a patient's airway via an opening in the patient's neck in order to treat acute conditions or to perform an elective procedure. The acute conditions may involve maxillofacial injuries, rapidly enlarging masses (e.g., head masses, neck masses, and the like), and/or airway inflammation. The elective procedures may involve planned laryngectomies, respiratory therapy (e.g., weaning patients from prolonged mechanical ventilators support), and removing airway obstructions (e.g., secretions). By way of example, tracheostomies are often performed to bypass an obstructed upper airway, to clean airways, and/or to more effectively deliver oxygen to the lungs.

In a tracheostomy, an opening is formed in a patient's neck to gain access to the trachea. A tracheostomy tube is then inserted through the opening and positioned within the trachea. Ventilation can be sustained by connecting the tracheostomy tube to a positive pressure ventilation device, such as a manual or mechanical ventilation device. Unfortunately, a patient being weaned from these types of positive pressure ventilation devices is often vulnerable to atelectasis and pneumonia. Respiratory therapy can be used to avoid these unwanted conditions while the patient is transitioned off of breathing support. However, the most effective forms of respiratory therapy are unavailable to tracheostomized patients.

Respiratory therapy often includes incentive spirometry for improving lung function (e.g., promoting deep inspiration), preventing atelectasis, preventing pneumonia, and the like. For example, incentive spirometry may keep a patient's lungs active while the patient recovers from procedures that involve a tracheostomy. Typically, a mouthpiece of the incentive spirometer is placed in the patient's mouth. The patient then breathes in to trigger the incentive spirometer, which is capable of measuring the volume of air drawn into the lungs. After filling the lungs with air, the patient removes the mouthpiece and exhales. Unfortunately, this type of incentive spirometer is unsuitable for use by a tracheostomized patient, because the patient, with the tracheostomy tube, is unable to properly breathe through the mouth.

BRIEF SUMMARY

In certain embodiments, a respiratory circuit is used by a tracheostomized patient to benefit from respiratory care afforded by incentive spirometry while also allowing pulmonary function testing. The respiratory circuit can be used to transition the tracheostomized patient off of mechanical ventilation, to help bedridden patients with permanent tracheostomies breathe, and the like. Incentive spirometry and pulmonary function testing may be conveniently performed periodically or continuously without removing the tracheostomy tube.

The respiratory circuit can include a flow controller that fluidly couples an incentive spirometer to a tracheostomy tube. The flow controller allows a tracheostomized patient to perform spirometry by connecting the flow controller to different types of incentive spirometers. In some embodiments, the flow controller comprises a flow control adapter configured to be removably coupled or to be permanently coupled to a tracheostomy tube and an incentive spirometer. The flow control adapter can have an expiratory port through which expiratory air flows to additional component(s). In some embodiments, the expiratory port is fitted with a valve, such as a one-way valve. The adapter can also have an endotracheal tube fitting, such as a port, configured to couple indirectly or directly to the tracheostomy tube. The flow controller can function without any manual operation by the user.

In some embodiments, a flow control adapter includes a subject port adapted to couple to a tracheostomy tube, an inspiratory port adapted to couple to an incentive spirometer, and an expiratory port. The flow control adapter further includes an adapter body and a one-way valve. The adapter body defines an inspiratory fluid flow path between the inspiratory port and the subject port and defines an expiratory fluid flow path between the subject port and the expiratory port during use. The one-way valve substantially prevents air that flows generally along the inspiratory fluid flow path from flowing through the expiratory port during inspiration and allows air that flows generally along the expiratory fluid flow path to flow through the expiratory port during expiration.

The one-way valve is in a closed position during inspiration and at least partially open position during expiration. In some embodiments, the one-way valve moves from the closed position to the at least partially open position in response to a pressure change produced by the patient's breathing. This pressure change can be at least about 5 cm $H_2O$, 10 cm $H_2O$, 15 cm $H_2O$, or 20 cm $H_2O$, or ranges encompassing such pressures generated between inspiration and expiration. In some embodiments, the one-way valve comprises a flow control element that is biased towards the closed position such that the one-way valve is closed when a pressure within the adapter body is below an expiratory pressure. When the patient inhales, the flow control element remains in the closed position. The flow control element moves towards the open position in response to pressure increases associated with expiration.

In some embodiments, a breathing circuit comprises an incentive spirometer, a tracheostomy tube, a pulmonary testing device, and a flow control adapter. The flow control adapter has an inspiratory mode to fluidly couple the incentive spirometer to the tracheostomy tube while substantially preventing fluid communication between the pulmonary testing device and the incentive spirometer. The flow control adapter further has an expiratory mode to fluidly couple the tracheostomy tube to the pulmonary testing device. In some embodiments, the flow control adapter automatically alternates between the inspiratory mode and the expiratory mode based upon the breathing cycle.

The flow control adapter, in some embodiments, is in the inspiratory mode when a vacuum is drawn by the patient. The flow control adapter changes from the inspiratory mode to the expiratory mode in response to a pressure change in the flow control adapter. Such a pressure change is at least about 5 cm $H_2O$, 10 cm $H_2O$, 15 cm $H_2O$, or 20 cm $H_2O$, or ranges encompassing such pressures. The pressure change is a pressure differential between inspiration and expiration. In some embodiments, the flow control adapter includes at least one valve that is in the closed position during the inspiratory mode and another valve that is in the closed position during the expiratory mode. The flow control adapter can be a handheld portable component that is disposable or reusable. The flow control adapter can be plugged into different types of breathing circuits.

In some embodiments, a method comprises passing inspiratory air away from an incentive spirometer, through a flow control adapter, and into a tracheostomy tube while an expiratory valve of the flow control adapter is in a closed position. Expiratory air is delivered away from a subject connected to the tracheostomy tube and into the flow control adapter. The expiratory air within the flow control adapter is delivered past the valve is in an open position. The expiratory air that has been delivered past the valve is delivered to a pulmonary testing device.

In some embodiments, substantially all of the inspiratory air delivered through the flow control adapter and into the tracheostomy tube passes through an inspiratory port of the flow control adapter. For example, at least 80%, 90%, or 95% by volume of such inspiratory air is delivered through the flow control adapter. The inspiratory port is coupled to the incentive spirometer. In some embodiments, substantially all of the expiratory air flowing out of the flow control adapter during expiration has flowed past the valve in the open position. In further embodiments, the valve is movable from the closed position to an open position in response to a pressure change associated with breathing of a subject connected to the tracheostomy tube.

In some embodiments, a method comprises providing a breathing circuit including an incentive spirometer, a flow control device, and a pulmonary testing device. Incentive spirometry testing can be performed while a patient inhales, and the flow control device inhibits inspiratory air flow towards the pulmonary testing device. In certain embodiments, the flow control device substantially prevents inspiratory air flow towards the pulmonary testing device. The pulmonary testing device is used to perform pulmonary tests while the patient exhales causing expiratory air flow through the flow control device towards the pulmonary testing device. In some embodiments, incentive spirometry testing can be performed to evaluate the health of the patient's lungs by mimicking natural sighing or yawning. The incentive spirometry testing can include, without limitation, increasing transpulmonary pressure, increasing inspiratory volumes, improving inspiratory lung function, or affecting pulmonary hyperinflation.

In other embodiments, the flow control adapter includes a one-way valve that is configured to move from a closed state to an at least partially opened state in response to pressure produced during breathing. In certain embodiments, the one-way valve comprises at least one flow control element that is biased towards the closed state such that the one-way valve is closed when the pressure within a chamber of the flow control adapter is below a threshold pressure. If the flow control element includes a pair of flexible flaps, the flaps can be brought together to substantially prevent airflow.

In yet other embodiments, a breathing circuit comprises a first pulmonary device, a second pulmonary device, a tracheostomy tube, and means for controlling air flow. The means for controlling air flow having an inspiratory mode to fluidically couple the first pulmonary device to the tracheostomy tube while substantially preventing fluid communication between the second pulmonary device and at least one of the tracheostomy tube and the first pulmonary device. In certain embodiments, the first pulmonary device is an incentive spirometer. The second device can be testing equipment. The means for controlling air flow has an expiratory mode to fluidically couple the tracheostomy tube to the second pulmonary device.

BRIEF DESCRIPTION OF THE SEVERAL VIEWS OF THE DRAWINGS

In the drawings, identical reference numbers identify similar elements or acts.

DETAILED DESCRIPTION

Figure 1:
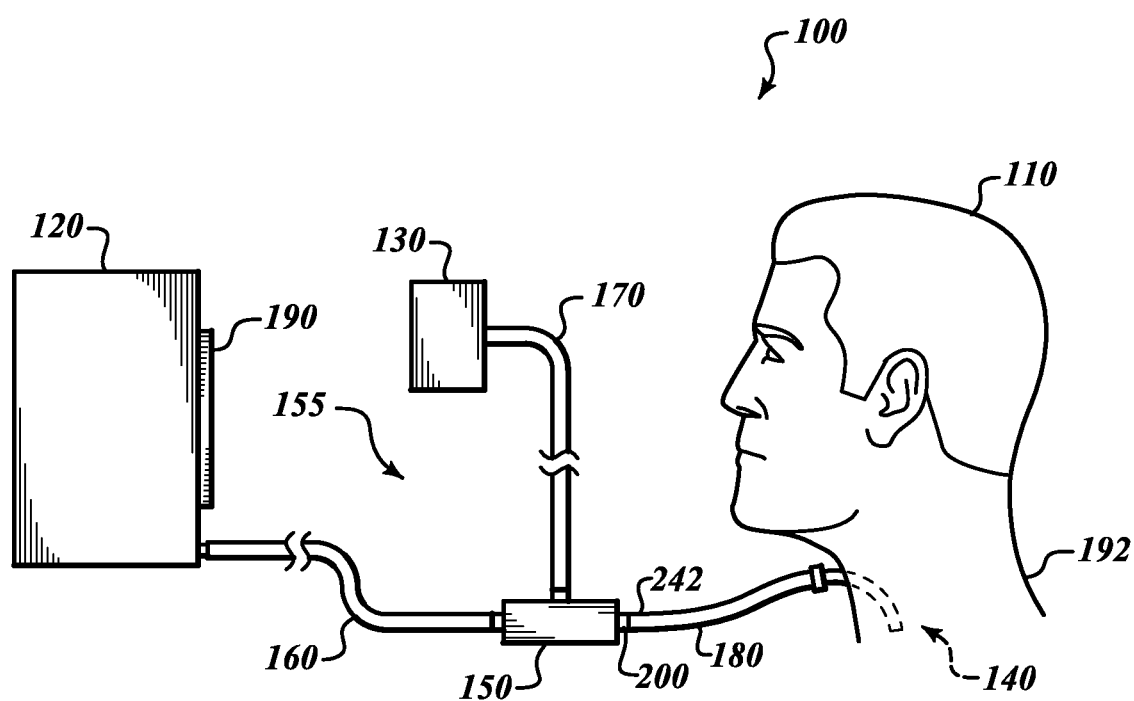
FIG. 1 is a pictorial view of a respiratory circuit and a tracheostomized subject.

FIG. 1 shows a respiratory circuit 100 coupled to a tracheostomized subject 110. The illustrated respiratory circuit 100 can be used to perform different types of continuous or periodic spirometry (e.g., incentive spirometry), pulmonary function testing, combinations thereof, and the like. As used herein, the term "respiratory circuit" includes, without limitation, any apparatus through which a subject may breathe. A respiratory circuit may include, without limitation, one or more flow controllers, flow control adapters, spirometers, tubes (e.g., tracheostomy tubes, endotracheal tubes, and the like), fluid lines, breathing circuits, masks, mouthpieces, nebulizers, drug delivery devices, combinations thereof, or the like. As the subject 110 breathes, the respiratory circuit 100 can alternatingly perform spirometry and lung function testing. The air flow generated by the subject 110 operates the components of the circuit 100.

The respiratory circuit 100 generally includes an incentive spirometer 120, a pulmonary testing device 130, an intraluminal tube 140 (illustrated as a tracheostomy tube), and a flow control adapter 150. The flow control adapter 150 provides fluid communication between the tracheostomy tube 140 and both the incentive spirometer 120 and the pulmonary testing device 130. Various types of fluids can flow through the respiratory circuit 100. Exemplary non-limiting fluids include, without limitation, one or more gases (e.g., air), liquids (e.g., liquid medicants), or gas/liquid mixtures (e.g., air carrying medicants such as nebulized or aerosolized solutions), as well as other flowable substances suitable for delivery to the subject.

The flow control adapter 150 directs air to different components during different portions of the breathing cycle. The air flow provided by the subject 110 causes operation of the flow control adapter 150 for consistent performance. For example, when the subject 110 inhales, air from the incentive spirometer 120 is drawn through the respiratory circuit 100 and into the lungs of the subject 110. The flow control adapter 150 isolates the pulmonary testing device 130 from this inspiratory flow of air such that the subject 110 performs incentive spirometry. When the subject 110 exhales, air is expelled from the lungs and is delivered into the flow control adapter 150. The flow control adapter 150 directs the expiratory flow of air towards the pulmonary testing device 130. The pulmonary testing device 130 receives the expiratory flow of air to perform testing. In this manner, the tracheostomized subject 110 can use the incentive spirometer 120 for incentive spirometry and the pulmonary testing device 130 for testing lung function. Because the flow control adapter 150 automatically directs air flow, the respiratory circuit 100 can be used while the subject 110 performs activities, rests, sleeps, or the like.

The respiratory circuit 100 further includes a network of fluid lines 155 that fluidically interconnects circuit components. The illustrated network of fluid lines 155 includes an inspiratory line 160 that extends between the incentive spirometer 120 and the flow control adapter 150, an expiratory line 170 that extends between the pulmonary testing device 130 and the flow control adapter 150, and a subject line 180 that extends between the tracheostomy tube 140 and the flow control adapter 150. As used herein, the term line includes, without limitation, one or more tubes, conduits, or other components through which fluid flows to provide fluid communication between two or more components. In some embodiments, a line is a plurality of conduits connected together to define a single flow path between two components. In some embodiments, a line includes one or more connectors, fittings, valves, and the like positioned at various locations along its length. In some embodiments, a line is a single conduit connecting two components.

The incentive spirometer 120 can be used in a wide range of different types of respiratory therapy. In some embodiments, the incentive spirometer 120 is operable to generally mimic one or more normal respiratory functions, such as sighing, yawning, or the like, by encouraging the subject 110 to take long, slow, deep breaths. During inspiration, positive visual feedback can be provided to the subject 110 based on, at least in part, target flow rates, volume of inhaled air, desired lung expansion/contraction, and the like. An indicator 190 (e.g., a screen, a display, a monitor, or the like) of the incentive spirometer 120 outputs visual feedback viewable by the subject 110. Based on the feedback, the subject 110 can adjust the breathing cycle. The incentive spirometer 120 can be any of a wide range of conventional incentive spirometers known in the art.

The pulmonary testing device 130 is used to evaluate pulmonary function. The illustrated pulmonary testing device 130 is a spirometer capable of obtaining the forced expiratory volume in the first second ("FEV1"), forced expiratory volume in the first six seconds ("FEV6"), or forced vital capacity ("FVC"), as well as other lung function tests or measures associated with pulmonary function, such as respiratory pressures (e.g., maximum expiratory pressures). FEV1 is the volume of air the subject 110 can force out in one second after taking a deep breath. FEV6 is the volume of air the subject 110 can force out six seconds after taking a deep breath. The type and configuration of the pulmonary testing device 130 can be selected based on the respiratory therapy programs to be performed. For example, the pulmonary testing device 130 may include, without limitation, one or more of ventilators, respirators, breathing machines, flow meters, and the like.

The tracheostomy tube 140 keeps the stoma and trachea at least partially open. In some embodiments, the tracheostomy tube 140 has a longitudinal length in a range of about 2 inches to about 4 inches and is made, in whole or in part, of one or more metals, plastics, rubbers, and the like. Other dimensions and materials can also be used. The tracheostomy tube 140 of FIG. 1 has been inserted through an opening in a neck 192 and advanced into and through at least a portion of the trachea.

In other embodiments, the tube 140 is an endotracheal tube or other type of fluid line (rigid or flexible) suitable for delivery into anatomical features of the respiratory system, such as the nose, mouth, or the like. Various types of features can be incorporated into the tube 140. For example, the tube 140 can include a plurality of lumens, inflatable members (e.g., compliant balloons), connectors, sensors, sealing members, and the like. As such, the respiratory circuit 100 can include a wide range of well known intraluminal tubes.

Figure 2:
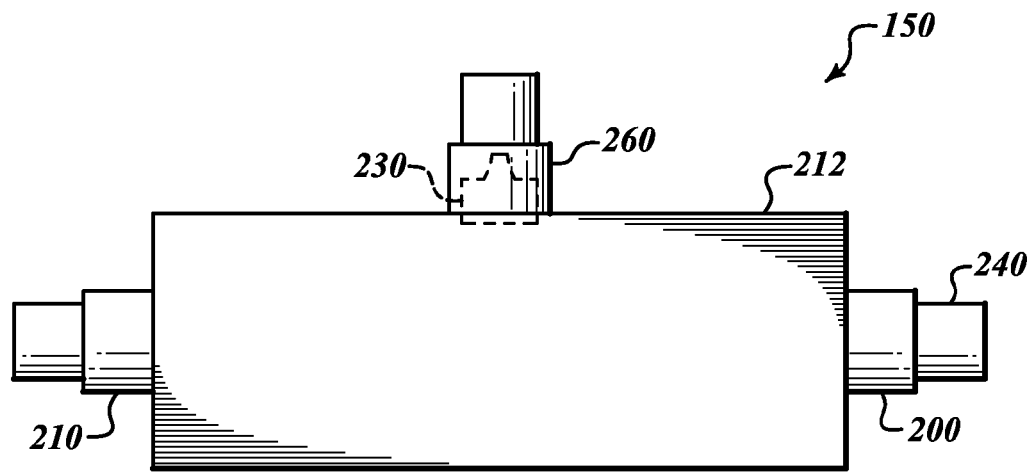
FIG. 2 is an elevational side view of a flow control adapter of the respiratory circuit of FIG. 1.
Figure 3:
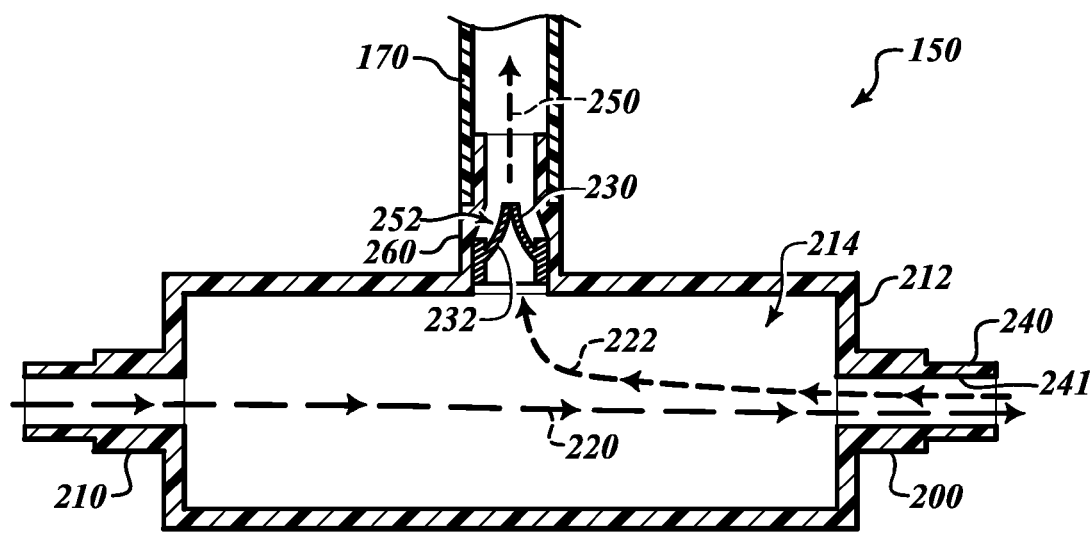
FIG. 3 is a cross-sectional view of the flow control adapter of FIG. 2.

Referring to FIGS. 2 and 3, the flow control adapter 150 includes a subject port 200 configured to be coupled (directly or indirectly) to the subject line 180, an inspiratory port 210 configured to be coupled to the inspiratory line 160, an expiratory port 260, and a main body 212 connecting the subject port 200 to the inspiratory port 210. The main body 212 defines a chamber 214 that defines an inspiratory fluid flow path 220 (illustrated in dashed line) and an expiratory fluid flow path 222 (illustrated in dashed line). The inspiratory fluid flow path 220 extends between the inspiratory port 210 and the subject port 200. The expiratory fluid flow path 222 extends between the subject port 200 and the expiratory port 260.

The subject port 200, inspiratory port 210, and expiratory port 260 can be generally similar to each other and, accordingly, the following description of one of the ports applies equally to the others, unless indicated otherwise. The subject port 200 is an outwardly extending plug defining a passageway 241 and a nipple 240 for connecting to and forming a fluid tight fit (e.g., an interference fit) with an end 242 of the subject line 180, as shown in FIG. 1. In other embodiments, the subject port 200 is an aperture in the main body 212. Such subject port 200 can have internal threads that mate with external threads at the end 242 of the subject line 180. In yet other embodiments, the subject port 200 is a fluid line monolithically formed with the main body 212.

In the illustrated embodiment of FIG. 1, the subject port 200 is coupled directly to the end 242. In other embodiments, the subject port 200 is indirectly coupled to the end 242. For example, a component can be interposed between and can connect the subject port 200 and the end 242. The component can include, without limitation, a flow regulator, connector, sensor, fitting, combinations thereof, and the like.

Referring again to FIG. 3, a valve 230 controls the flow of air between the expiratory line 170 and the chamber 214. The valve 230 can be a one-way valve that allows flow of air in one direction and at least substantially prevents flow of air in the opposite direction. The illustrated one-way valve 230 is movable between a closed position and a partially or fully open position. In the closed position, the valve 230 inhibits, limits, or at least substantially prevents flow from the chamber 214 into the expiratory line 170. The valve 230 in the partially or fully open position allows air to flow along the expiratory fluid flow path 222 and into the expiratory line 170, as indicated by an arrow 250 of FIG. 3.

One-way valves include, but are not limited to, duckbill valves, check valves, cross-slit valves, umbrella valves, or the like. These types of one-way valves can open and closed based on air pressures, air flows, or the like within the respiratory circuit 100. The one-way valve 230 illustrated in FIG. 3 is a duckbill valve positioned along a passageway 252 of the expiratory port 260. In other embodiments, the valve 230 is a butterfly valve, ball valve, globe valve, or other type of flow regulating valve and may be manually or automatically opened and closed.

The valve 230 includes a valve element 232 movable between an open position and a closed position, although the valve element 232 is biased towards the closed position. When the pressure in the chamber 214 is sufficiently high, the valve element 232 becomes partially or fully open. When the pressure in the chamber 214 is decreased a sufficient amount, the valve element 232 moves to the closed position. In this manner, the valve element is operated to fluidically isolate the testing device 130 from both the incentive spirometer 120 and the subject 110 during certain portions of the breathing cycle.

With continued reference to FIGS. 2 and 3, the flow control adapter 150 can have a one-piece or multi-piece construction. Various types of machining processes, molding processes (e.g., injection molding, compression molding, and the like), and milling processes can be used to manufacture the main body 212, as well as the ports 200, 210, 260. The valve 230 can be temporarily or permanently coupled to the expiratory port 260 using one or more adhesives, welds, fasteners (e.g., screws, pins, and the like), threads, combinations thereof, or the like.

Figure 4:
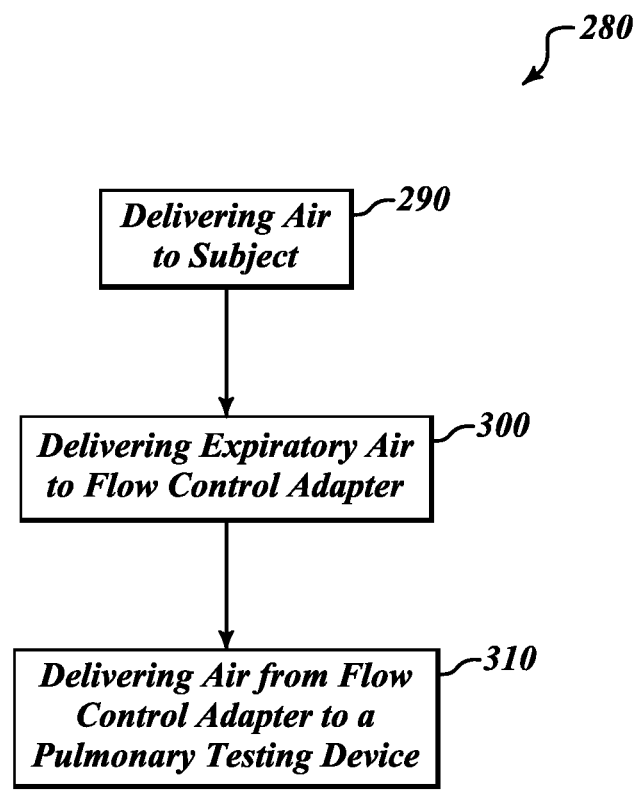
FIG. 4 is a flow chart of one method of using a respiratory circuit.
Figure 5A:
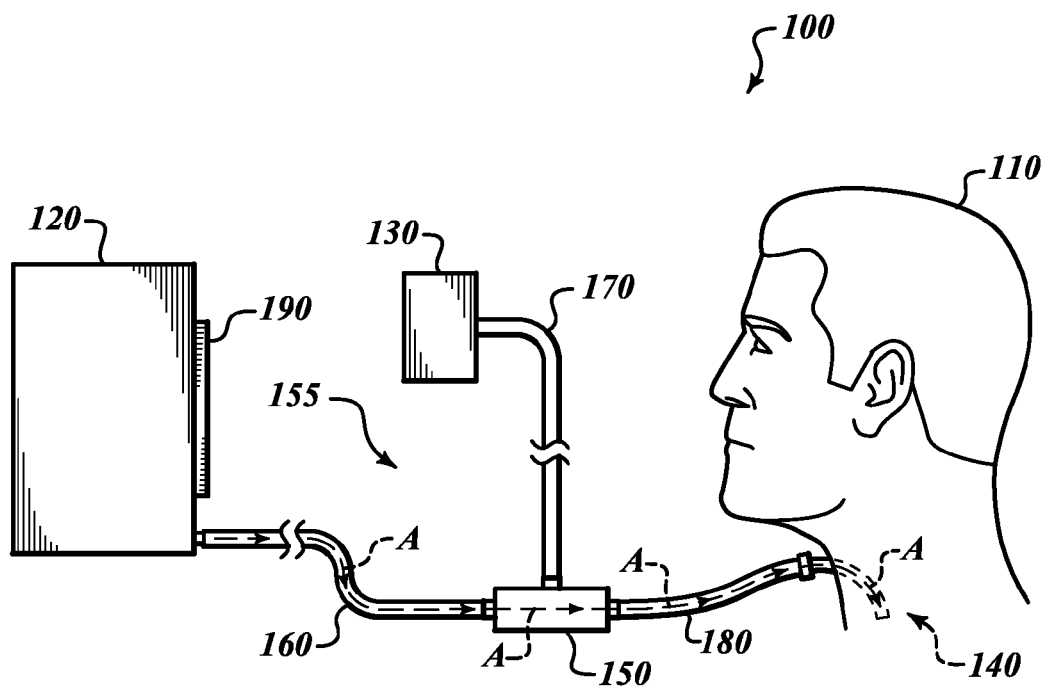
FIG. 5A is a pictorial view of a respiratory circuit during inspiration.

FIG. 4 is a flow chart of one method 280 of using the respiratory circuit 100 of FIG. 1. The subject 110 can perform breathing cycles to alternatively operate the incentive spirometer 120 and the pulmonary testing device 130. At 290, the subject 110 inhales so as to draw a vacuum. Air from the incentive spirometer 120 flows through the respiratory circuit 100 to the subject 110. As shown in FIG. 5A, inspiratory air A flows through the inspiratory line 160 and into the flow control adapter 150 via the inspiratory port 210. The air A passes along the inspiratory fluid flow path 220 within the flow control adapter 150, while the closed valve 230 prevents air flow into the expiratory line 170. In some embodiments, substantially all of the inspiratory air A flowing through the inspiratory port 210 flows out of the subject port 200. In certain embodiments, at least 80% by volume, 90% by volume, or 95% by volume of the inspiratory air A flows out of the subject port 200. Other volumes of air can also flow through the inspiratory port 210 and out of the subject port 200, if needed or desired. In this manner, the flow control adapter 150 provides fluid communication between the lines 160, 180 without any appreciable pressure loss during inhalation. The inspiratory air A flows out of the subject port 200 and proceeds along the subject line 180 and into the tracheostomy tube 140, and ultimately into the lungs of the subject 110. During this process, the subject 110 can view the visual indicator 190, if needed or desired.

Figure 5B:
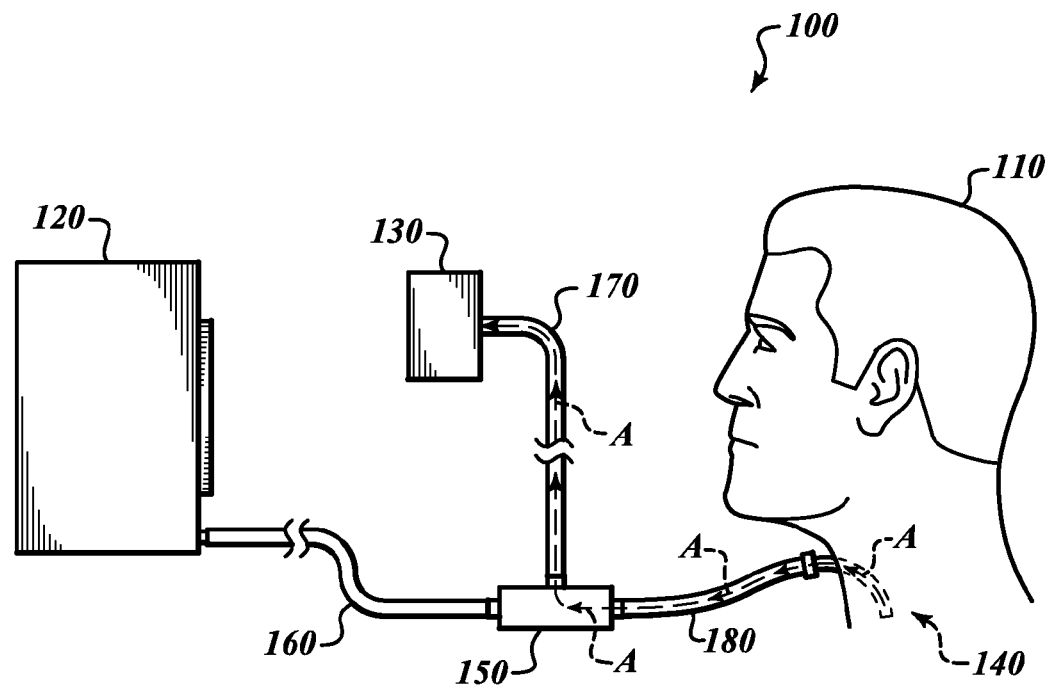
FIG. 5B is a pictorial view of the respiratory circuit of FIG. 5A during expiration.

After filling the lungs with air, the subject 110 begins to exhale. At 300 of FIG. 4, the subject 110 exhales expiratory air that is delivered to the flow control adapter 150. As shown in FIG. 5B, oxygen depleted expiratory air A flows through the tracheostomy tube 140 and the subject line 180 and into the flow control adapter 150. The incentive spirometer 120 can have an internal valve, such as a one-way valve, that prevents air flow through the inspiratory line 160 during expiration. The subject 110 therefore causes a pressure increase in the flow control adapter 150 so as to open the valve 230.

At 310, the flow control adapter 150 delivers the expiratory air A to the pulmonary testing device 130 via the expiratory line 170. As shown in FIG. 3, the expiratory air A flows through the open valve 230, out of the expiratory port 260, and into the expiratory line 170. The air A then flows along the expiratory line 170 into the pulmonary testing device 130 in order to evaluate lung function. After completing exhalation, the subject 110 can inhale again to cause the open valve 230 to close to reestablish fluid communication with the incentive spirometer 120.

Figure 6:
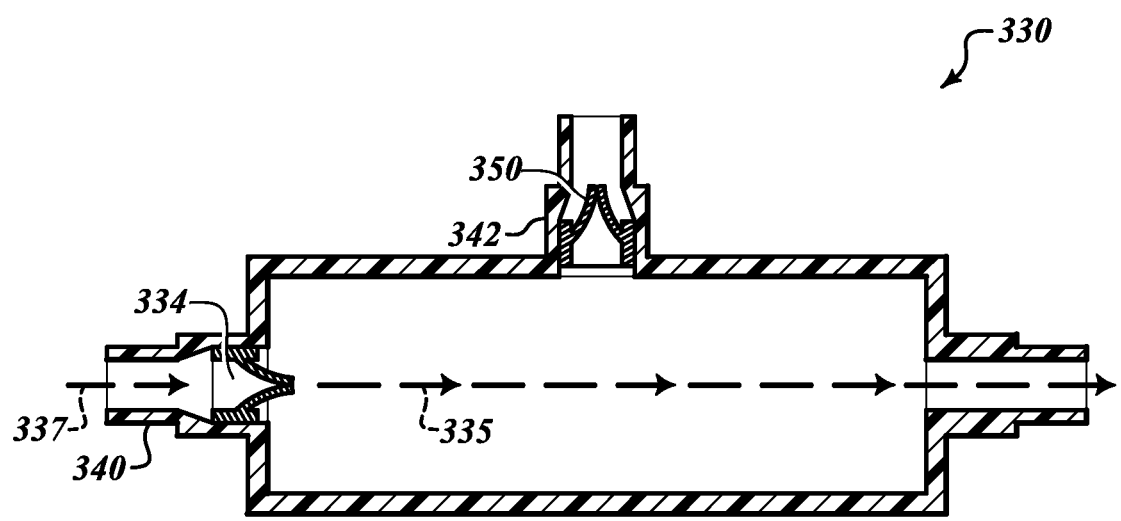
FIG. 6 is a cross-sectional view of a flow control adapter having a pair of valves.

FIG. 6 shows a flow control adapter 330 that is generally similar to the flow control adapter 150 discussed in connection with FIGS. 1 to 5B, except as detailed further below. The flow control adapter 330 includes a valve 334 for regulating the flow of air through an inspiratory port 340. During inhalation, air flows through the partially or fully open valve 334 in the direction indicated by the arrow 337. The air flows along an inspiratory fluid flow path 335 (shown in dashed line) through the flow control adapter 330. Exhalation causes the valve 334 to become closed in order to at least partially block the inspiratory port 340, thereby ensuring that substantially all of the expiratory air (e.g., at least 90% or 95% by volume of the air) flows through an expiratory port 342.

Figure 7:
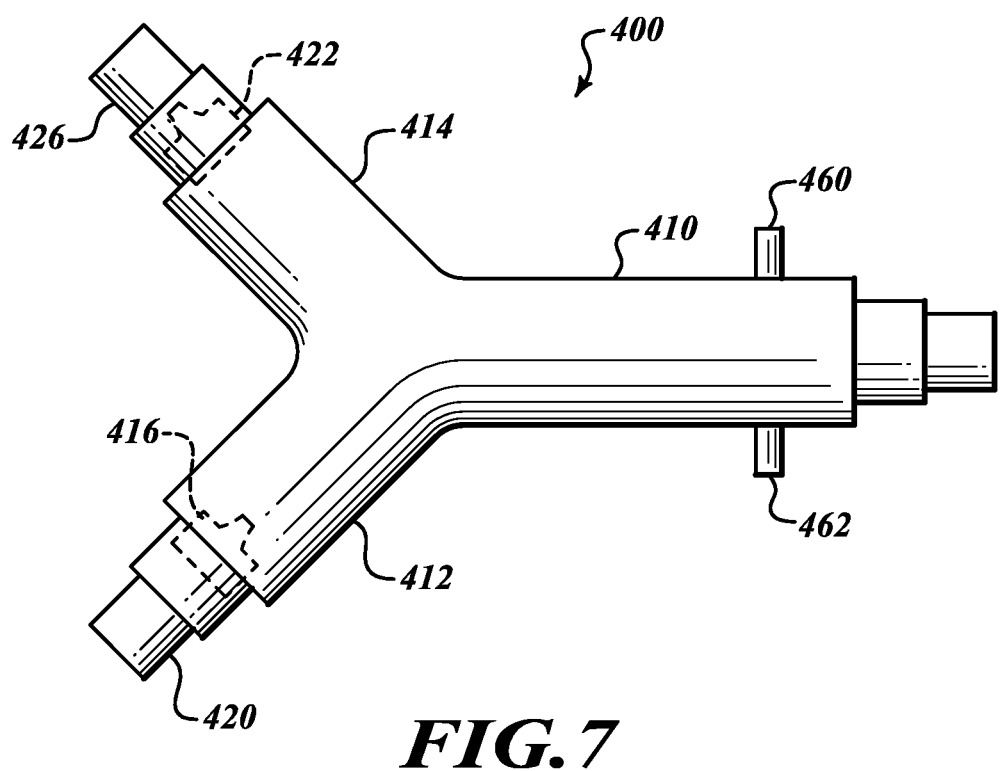
FIG. 7 is an elevational view of a flow control adapter, in accordance with another embodiment.

The flow control adapters discussed in connection with FIGS. 1-6 have generally T-shaped configurations. However, flow control adapters can have other configurations. FIG. 7 shows a flow control adapter 400 that has a generally Y-shaped configuration, as viewed from above. The flow control adapter 400 includes an inspiratory section 412 and an expiratory section 414 angled with respect to the section 412. A valve 416 (shown in dashed line) is positioned within the inspiratory section 412 to control air flow through an inspiratory port 420 carried by the inspiratory section 412. A valve 422 (shown in dashed line) is positioned within the expiratory section 414 to control air flow through an expiratory port 426 carried by the expiratory section 414.

Figure 8:
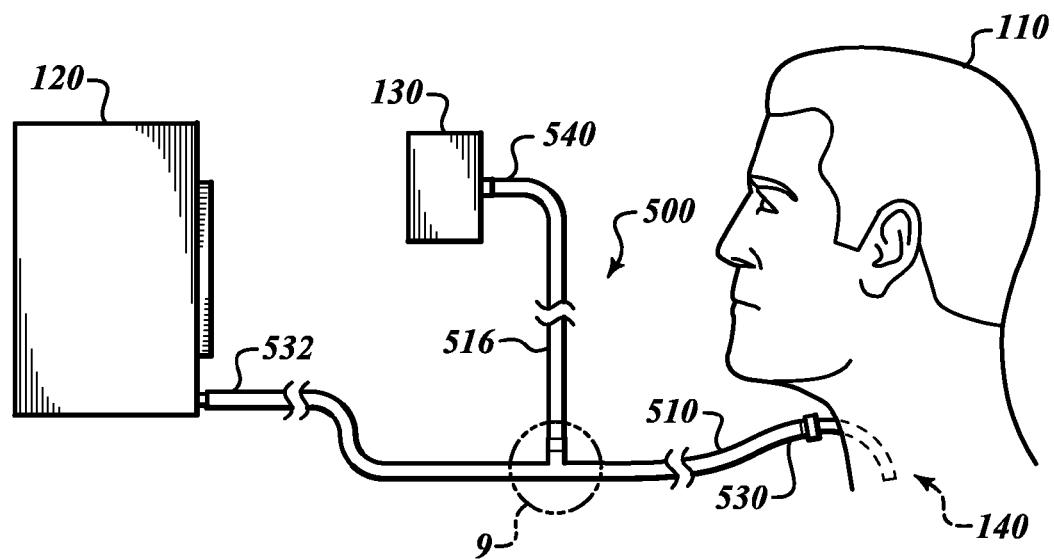
FIG. 8 is a pictorial view of a respiratory circuit and a tracheostomized patient, in accordance with one embodiment.
Figure 9:
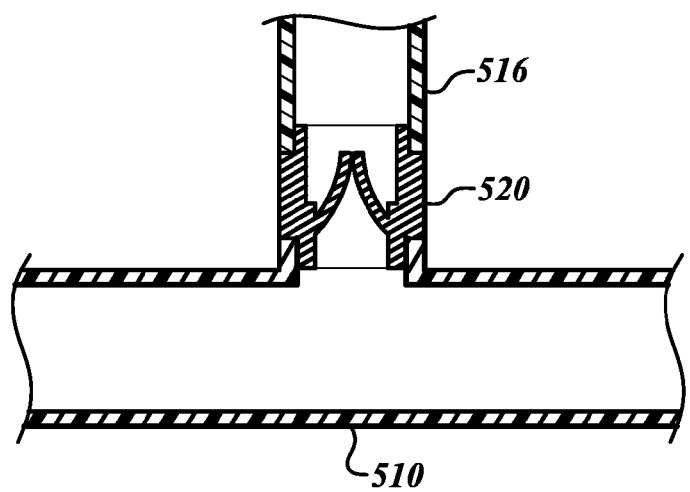
FIG. 9 is a detailed view of the respiratory circuit of FIG. 8.

FIG. 8 illustrates a flow control adapter 500 including a network of fluid lines. The illustrated flow control adapter 500 includes a line 510 extending between the incentive spirometer 120 and the subject 110. An expiratory line 516 provides fluid communication between the line 510 and the pulmonary testing device 130. As shown in FIG. 9, a valve 520 is between the lines 510, 516. The valve 520 can be conveniently replaced or removed, if needed or desired.

Various types of connections can connect the lines 510, 516 to other components. With reference to FIG. 8, a subject port 530 of the flow control adapter 500 is directly coupled to the tracheostomy tube 140. An inspiratory port 532 is directly coupled to the incentive spirometer 120. The expiratory port 540 is directly coupled to the pulmonary testing device 130. In other embodiments, intermediate components (e.g., connectors, flow regulators, or the like) are between the flow control adapter 500 and other components and/or the subject 110.

Figure 10:
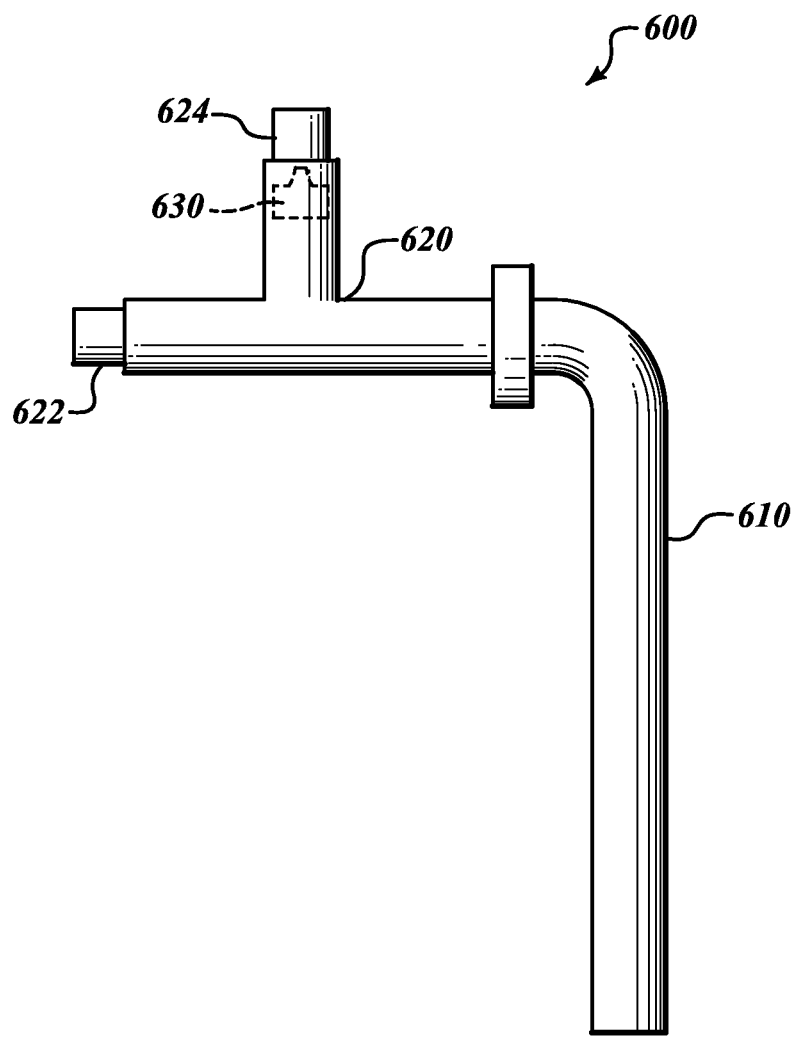
FIG. 10 is an elevational side view of a flow control adapter that includes a tracheostomy tube.

The flow control adapters described herein can be incorporated into various components of a respiratory circuit. FIG. 10 shows a flow control adapter 600 that includes a tube 610, illustrated as a tracheostomy tube. The flow control adapter 600 includes a T-shaped section 620 that fluidly connects an inspiratory port 622 to an expiratory port 624. A valve 630 (shown in dashed line) is positioned within the T-shaped section 620.

The flow control adapters can be utilized with sensing components or devices. For example, one or more ports can be incorporated into the flow control adapters described herein to evaluate one or more parameters of interest, such as air temperatures, air pressures, composition of inhaled/exhaled air, flow velocities, and the like. By way of example, the flow control adapter 400 of FIG. 7 includes a temperature monitoring port 460 for connecting to temperature sensing components, such as devices capable of monitoring the temperature of the air passing through the flow control adapter 400. The flow control adapter 400 also includes a pressure monitoring port 462 for connecting to pressure sensing components or devices.

Unless the context requires otherwise, throughout the specification and claims which follow, the word "comprise" and variations thereof, such as, "comprises" and "comprising" are to be construed in an open, inclusive sense, that is as "including, but not limited to."

As used in this specification and the appended claims, the singular forms "a," "an," and "the" include plural referents unless the context clearly dictates otherwise. Thus, for example, reference to a breathing circuit including "a line" includes a single line, or two or more lines. It should also be noted that the term "or" is generally employed in its sense including "and/or" unless the context clearly dictates otherwise.

Various changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system for performing spirometry and pulmonary function testing comprising:
 a flow control adapter, an incentive spirometer, a tracheostomy tube and an exhalation spirometer that measures forced expiratory volume, the flow control adapter further comprising a subject port adapted to be in fluid communication with an airway of a tracheostomized patient and directly coupled to the tracheostomy tube, an inspiratory port directly coupled to the incentive spirometer, an expiratory port coupled to the exhalation spirometer, and an adapter body that defines an inspiratory fluid flow path between the inspiratory port and the subject port and that defines an expiratory fluid flow path between the subject port and the expiratory port during use, the adapter body including:
 an inspiratory one-way valve positioned within the adapter body and coupleable to the inspiratory port such that the inspiratory one-way valve substantially prevents air that flows substantially along the inspiratory fluid flow path from flowing through the inspiratory port during expiration; and
 an expiratory one-way valve positioned within the adapter body and coupleable to the expiratory port such that the expiratory one-way valve allows air flowing substantially along the expiratory fluid flow path to flow through the expiratory port during expiration.

2. The system of claim 1, wherein the expiratory one-way valve is configured to be in a closed position during inspiration and at least partially open during expiration.

3. The system of claim 1, wherein the expiratory one-way valve moves from a closed state to an at least partially open state in response to a pressure produced during expiration.

4. The system of claim 3, wherein the expiratory one-way valve comprises a flow control element that is biased towards the closed state such that the one-way valve is closed when a pressure within the adapter body is below an expiratory pressure.

5. The system of claim 1, wherein the expiratory one-way valve is positioned within an expiratory passageway of the expiratory port.

6. The system of claim 5, wherein the expiratory one-way valve is fixedly coupled to a wall of the expiratory port defining the expiratory passageway.

7. The system of claim 6 wherein the adapter body comprises a unitary hollow body and, wherein, the inspiratory one-way valve is fixedly coupled to a wall of the inspiratory port defining an inspiratory passageway.

8. The system of claim 1 wherein the flow control adapter includes a temperature sensing port coupleable to a temperature sensing device and a pressure sensing port coupleable to a pressure sensing device.

9. A breathing circuit comprising:
 an incentive spirometer;
 a tracheostomy tube adapted to be coupled to a tracheostomized patient;
 an exhalation spirometer that measures forced expiratory volume; and
 a flow control adapter having an adapter body that includes an inspiratory one-way valve and an expiratory one-way valve secured within the adapter body, the adapter body having an inspiratory port directly coupled to the incentive spirometer and a subject port directly coupled to the tracheostomy tube, the flow control adapter having an inspiratory mode controlled by the inspiratory and expiratory one-way valves to fluidically couple the incentive spirometer to the tracheostomy tube while substantially preventing fluid communication between the exhalation spirometer and at least one of the tracheostomy tube and the incentive spirometer, and the flow control adapter further having an expiratory mode controlled by the inspiratory and expiratory one-way valves to fluidically couple the tracheostomy tube to the exhalation spirometer while substantially preventing fluid communication between the incentive spirometer and at least one of the tracheostomy tube and the exhalation spirometer.

10. The breathing circuit of claim 9, wherein the flow control adapter is in the inspiratory mode when a sufficient vacuum is drawn by a subject connected to the tracheostomy tube, the flow control adapter moves from the inspiratory mode to the expiratory mode in response to a pressure change in the flow control adapter caused by the subject.

11. The breathing circuit of claim 9, wherein the adapter body of the flow control adapter defines an inspiratory flow path between the incentive spirometer and the tracheostomy tube and defines an expiratory flow path between the tracheostomy tube and an expiratory port of the flow control adapter, the expiratory port spaced apart from the inspiratory flow path and fluidically coupled to the exhalation spirometer.

12. The breathing circuit of claim 11, wherein the flow control adapter further comprises a subject port coupled to the tracheostomy tube and, wherein the inspiratory one-way valve is coupled to the inspiratory port such that the inspiratory one-way valve substantially directs air flow through the inspiratory port during inspiration and substantially prevents air flow through the inspiratory port during expiration.

13. The breathing circuit of claim 9, further comprising:
 a patient line coupling the tracheostomy tube to the flow control adapter.

* * * * *